United States Patent [19]
Chin

[11] Patent Number: 5,676,636
[45] Date of Patent: Oct. 14, 1997

[54] METHOD FOR CREATING A MEDIASTINAL WORKING SPACE

[75] Inventor: Albert K. Chin, Palo Alto, Calif.

[73] Assignee: Origin Medsystems, Inc., Menlo Park, Calif.

[21] Appl. No.: 668,827

[22] Filed: Jun. 24, 1996

Related U.S. Application Data

[63] Continuation of Ser. No. 279,290, Jul. 22, 1994, abandoned.

[51] Int. Cl.$^6$ ...................................................... A61B 17/02
[52] U.S. Cl. ........................... 600/204; 600/215; 600/235
[58] Field of Search ............................. 600/235, 204, 600/215, 210; 606/198

[56] References Cited

U.S. PATENT DOCUMENTS

| | | | |
|---|---|---|---|
| 1,618,261 | 2/1927 | Arbogast. | |
| 1,798,124 | 3/1931 | Hunn | 600/235 X |
| 1,947,649 | 2/1934 | Kadavy | 128/20 |
| 3,710,783 | 1/1973 | Jascalevich | 269/328 X |
| 3,774,596 | 11/1973 | Cook | 128/5 |
| 3,782,370 | 1/1974 | McDonald | 128/20 |
| 4,052,980 | 10/1977 | Grams et al. | 128/18 |
| 4,077,412 | 3/1978 | Moossun | 128/347 |
| 4,357,940 | 11/1982 | Muller | 128/303 R |
| 4,447,227 | 5/1984 | Kotsanis | 604/95 |
| 4,459,978 | 7/1984 | Kotsanis | 128/20 |
| 4,598,699 | 7/1986 | Garren et al. | 128/4 |
| 4,662,955 | 5/1987 | Fakrai | 128/20 |
| 4,709,697 | 12/1987 | Muller | 128/303 R |
| 4,744,363 | 5/1988 | Hasson | 128/331 |
| 5,113,846 | 5/1992 | Hiltebrandt et al. | 128/20 |
| 5,122,122 | 6/1992 | Allgood | 604/174 X |
| 5,152,279 | 10/1992 | Wilk | 128/17 |
| 5,163,949 | 11/1992 | Bonutti | 606/192 |
| 5,176,128 | 1/1993 | Andrese | 128/20 |
| 5,176,692 | 1/1993 | Wilk et al. | 606/151 |
| 5,183,033 | 2/1993 | Wilk | 128/20 |
| 5,188,630 | 2/1993 | Christaudias | 606/191 |
| 5,195,505 | 3/1993 | Josefsen | 128/20 |
| 5,195,506 | 3/1993 | Hulfish | 128/20 |
| 5,195,507 | 3/1993 | Bilweis | 604/97 |
| 5,197,948 | 3/1993 | Ghodsian | 604/30 |
| 5,197,971 | 3/1993 | Bonutti | 606/192 |
| 5,271,385 | 12/1993 | Bailey | 128/20 |
| 5,279,575 | 1/1994 | Sugarbaker | 604/174 |
| 5,280,782 | 1/1994 | Wilk | 128/20 |
| 5,289,817 | 3/1994 | Williams et al. | 128/20 |

FOREIGN PATENT DOCUMENTS

| | | | |
|---|---|---|---|
| 0 246 086 | 11/1987 | European Pat. Off. | A61B 17/02 |
| 0 531 710 A2 | 3/1993 | European Pat. Off. | A61B 1/00 |
| 85 16 296 | 9/1985 | Germany | A61B 17/02 |
| 91 02 759.4 | 7/1991 | Germany | A61B 17/02 |
| 91-04 383 | 7/1991 | Germany | A61B 17/02 |
| 92 02 305.3 | 6/1992 | Germany | A61B 19/00 |
| 014392 WO-A 91/14 | 10/1991 | WIPO | 600/204 |
| 392 | 10/1991 | WIPO | A61B 1/32 |
| WO 92/18056 | 10/1992 | WIPO | A61B 17/02 |

OTHER PUBLICATIONS

M.M. Gazayerli, "The Gazayerli Endoscopic Retractor Model 1," Surgical Laparoscopy and Endoscopy, vol. 1, No. 2, 1991, pp. 98–100.

Geza J. Jako & Stephen Rozsos, "Preliminary Report: Endoscopic Laser Microsurgical Removal of Human Gallbladder," J. Laparoendoscopic Surgery, vol. 1, No. 4, 1991.

*Primary Examiner*—Michael H. Thaler
*Attorney, Agent, or Firm*—Limbach & Limbach

[57] ABSTRACT

A mechanical lifting retractor is provided which increases working space in the chest for cardiac surgery by temporarily expanding the space between the rib cage and the pericardium. The lifting device has a pair of parallel right-angled retractors. Distal portions of the retractors are insertable in side-by-side parallel relation between a pair of adjacent ribs in the rib cage and into the mediastinal space between the ribs and sternum and the pericardium beneath them. The distal portions are pivotable into a lifting position in which they are separated by a rotational angle of approximately 180°. Following insertion of the distal portions into the mediastinal space, the distal portions are rotated into the lifting position and oriented in the sagittal plane such that each distal portion extends beneath one of the ribs. A lifting force is applied to the lifting retractor, causing the distal portions to engage the ribs and to lift the rib cage and thereby enlarging the mediastinal space. The lifting force is maintained for the duration of the surgical procedure.

8 Claims, 7 Drawing Sheets

METHOD FOR CREATING A MEDIASTINAL WORKING SPACE

The present application is a continuation of application Ser. No. 08/279,290, filed Jul. 22, 1994, now abandoned.

FIELD OF THE INVENTION

The present invention relates generally to the field of surgical retraction devices and, particularly, to the field of devices for optimizing working space in the chest for endoscopic cardiac surgery.

BACKGROUND OF THE INVENTION

Present techniques for providing surgical access to the heart and coronary arteries are highly invasive. Cardiac surgery is conventionally performed via a median sternotomy, a procedure in which the patient's skin is incised at the midline overlying the chest, and in which the sternum is divided longitudinally along its entire length. Access may be gained to the coronary arteries for bypass surgery, or to the heart valves for valve replacement, by forming an incision in the pericardium, the fibrous sac enclosing the heart. The cut edges of the sternum are retracted with metal retractors, exposing a large cavity to allow surgery to be performed on the heart.

Access to the heart for certain procedures may be gained using a subxiphoid incision, which provides an entrance into the abdominal cavity, and by a second incision through the diaphragm and the pericardium to provide entry from the abdominal cavity to the inferior aspect of the heart. Implantable cardiac pacemakers can be implanted using this approach. However, this technique does not provide sufficient exposure of the coronary arteries or heart valves to allow it to be used for coronary artery bypass surgery or cardiac valve replacement.

Some procedures may be performed using a suprasternal approach, during which a rigid endoscope is inserted into the mediastinal cavity (the cavity which contains the heart and the other organs positioned between the pleural sacs) through a small incision formed above the sternum. However, this technique is useful for a limited number of procedures, such as visualization of the mediastinal cavity (mediastinoscopy), and small procedures such as lymph node biopsy.

Access to the anterior extrapericardial space for closed cardiac massage in cardiac arrest may be gained using an intercostal approach. For this approach, an incision is formed in the space between the ribs adjacent the sternum. An inflatable ring is inserted through the incision and placed over the heart. The ring is inflated to compress the heart and to thereby circulate blood during cardiac arrest. Because the heart lies just beneath the sternum, very little working space exists for manipulation of the inflatable ring or for insertion of surgical instruments between the heart and the sternum and adjacent ribs.

Thoracoscopic techniques may allow access to the heart from a lateral approach, through the pleural cavity. Multiple incisions are formed in intercostal sites on one side of the chest. The lung on that side of the chest is collapsed, and the pleura is incised to give access to the heart in the mediastinum. Disadvantages of this approach include the increased instrument length required to reach the heart, and the lack of access to the anterior surface of the heart, which is covered by the sternum.

Since the subxiphoid, suprasternal, intercostal and thoracoscopic approaches provide limited access to the heart, researchers are presently considering endovascular substitutes for open heart surgery. For example, some researchers have reported animal studies in which a total endovascular approach was used to implant heart valves in piecemeal fashion in animals and to assemble the valves in situ. This approach has inherent technical difficulties; for example, the development of reliable valves capable of being assembled in situ. Even some conventional heart valves designed for open heart placement suffer from fatigue fracture problems.

SUMMARY OF THE INVENTION

The method and apparatus of the present invention utilize mechanical lifting of the rib cage to create a working cavity above the heart, so that cardiac surgery may be performed through a number of small incisions in the thoracic cavity. Use of this procedure eliminates the need for forming a large incision in the chest and for dividing the sternum.

A specialized retractor is inserted through an incision formed in the chest and is passed between a pair of ribs into the intercostal space overlying the heart. The preferred retractor has two retractor bars which are independently rotatable between an insertion position and a lifting position. In the insertion position, the retractor bars are positioned in close parallel relationship to enable their simultaneous insertion through the incision. Once the retractor bars are within the intercostal space, each is rotated through a rotational angle of approximately 90° in a direction opposite from the direction of rotation of the other retractor bar. The retractor bars are aligned in the sagittal plane, such that each bar contacts one of the ribs. The retractor bars are locked into the open position and the retractor is lifted by a powered lifting device, or it is lifted by hand and secured in an elevated position by means of a suspension system secured to the side rail of the operating table supporting the patient.

Alternative retractors include a single legged retractor or a fan retractor that opens to an acute angle. The retractors of the present invention are suitable for introduction through subxiphoid, suprasternal, or intercostal incisions.

DETAILED DESCRIPTION OF THE PREFERRED EMBODIMENT

Figure 1:
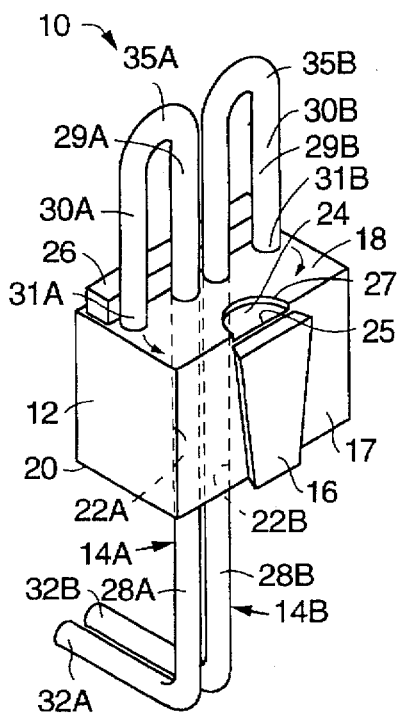
FIG. 1 is a perspective view of a first embodiment of an intercostal retractor according to the present invention, showing the retractor bars in the insertion position.

The retractor of the present invention is configured to engage with a portion of a patient's rib cage (i.e. with the sternum and/or one or more of the ribs) and to impart lifting force to the rib cage. In this manner, the intercostal space is used to create a working space between the heart and the rib cage by enlarging the mediastinal space (the space between the rib cage and pericardium), allowing visualization of the heart using an endoscope and further allowing manipulation of endoscopically placed surgical instruments.

Referring to FIGS. 1–6, a preferred intercostal retractor 10 is comprised of a lifting body 12, a pair of retractor arms 14a, 14b and a mounting device 16 for mounting the intercostal retractor 10 to a mechanical lifting arm, such as the one described in application Ser. No. 07/959,717, now abandoned, which is incorporated herein by reference.

The lifting body 12 is rectangular and has a superior face 18 and an inferior face 20. A pair of parallel throughbores 22a, 22b (FIG. 1) extend through the body 12 from the superior face 18 to the inferior face 20. The mounting device 16, which is preferably a dovetail connector configured to mate with a dovetail mount on the mechanical lifting arm (not shown), is attached to a side face 17 of the lifting body 12.

Figure 6:
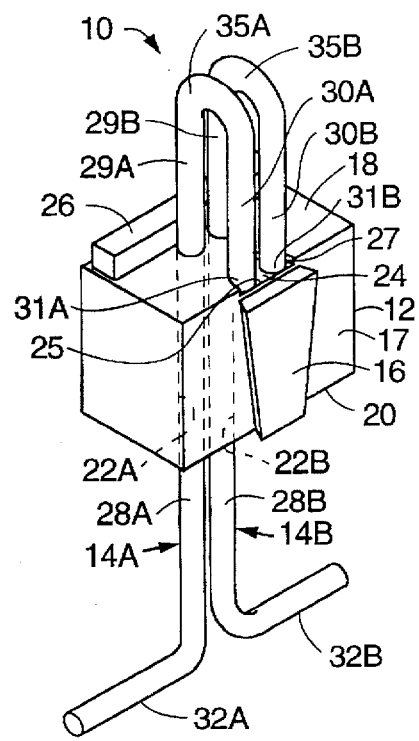
FIG. 6 is a perspective view of the intercostal retractor of FIG. 1, showing the retractor bars in the lifting position.

A position stop 26 is secured to the superior face 18 of the lifting block 12, adjacent to the throughbores 22a, 22b. This stop is preferably an elongate rectangular bar having an edge 33 (shown in FIG. 2) immediately adjacent to the throughbores 22a, 22b. A recessed locking groove 24 is formed into the superior face 18 of the lifting body 12. As shown in FIGS. 1 and 6, the locking groove 24 is semi-circular in shape, having an open side defined by a straight edge 25 centered along the side wall 17 of the lifting body 12 and an arcuate upstanding side defined by an edge 27 extending towards the position stop 26.

The retractor arms 14a, 14b have intermediate portions 28a, 28b partially disposed within the respective throughbores 22a, 22b of the lifting body 12. Proximal ends 29a, 29b, respectively, of intermediate portions 28a, 28b are contiguous with deployment bars 30a, 30b, at elbows 35a, 35b as shown in FIGS. 1 and 6. Tips 31a, 31b are located at the distalmost ends of the deployment bars 30a, 30b.

Retractor bars 32a, 32b are contiguous with and extend laterally from the intermediate portions 28a, 28b at the distal ends of the retractor arms 14a, 14b. When the device is positioned with the retractor arms 14a, 14b oriented vertically as shown in FIG. 1, each deployment bar 30a, 30b and the proximal end 29a, 29b of its respective retractor arm 14a, 14b lies in a vertical plane that is perpendicular to the vertical plane of its corresponding retractor bar 32a, 32b. The retractor bars 32a, 32b are preferably 2–3 cm in length.

The intermediate portions 28a, 28b are slidably and rotatably disposed within the throughbores 22a, 22b, respectively, such that rotation of the deployment bars 30a, 30b produces corresponding rotation of the retractor bars 32a, 32b. In this manner the retractor arms 14a, 14b are movable between an insertion position, shown in FIGS. 1–3, and a lifting position shown in FIGS. 4–6. In the insertion position, the retractor bars 32a, 32b are disposed in closely spaced generally parallel relationship, while and the deployment bars 30a, 30b are separated by a rotational angle of approximately 180°. In the lifting position the deployment bars 30a, 30b are in close parallel relationship and the retractor bars 32a, 32b are separated by an angle of approximately 180°.

As best shown in FIG. 6, the tips 31a, 31b slip into the locking groove 24 when the retractor arms 14a, 14b are moved into the lifting position. This provides resistance against rotational movement of the retractor arms 14a, 14b which might otherwise be caused by torsional forces received by the retractor arms 14a, 14b during lifting.

Figure 2:
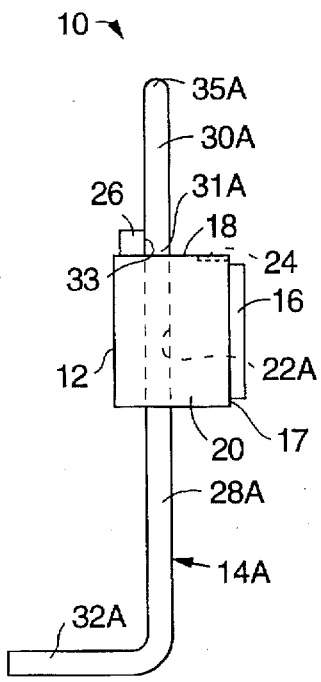
FIG. 2 is a side view of the intercostal retractor of FIG. 1.
Figure 3:
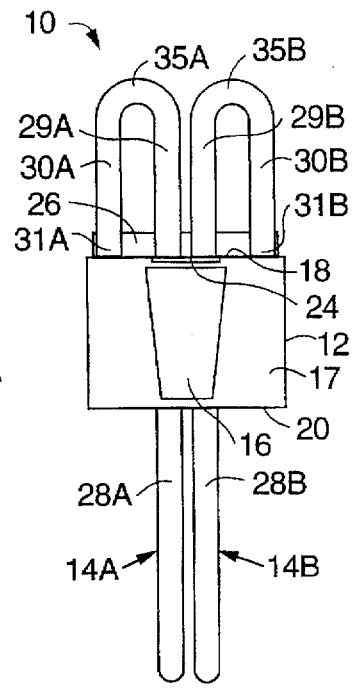
FIG. 3 is a front view of the intercostal retractor of FIG. 1.
Figure 4:
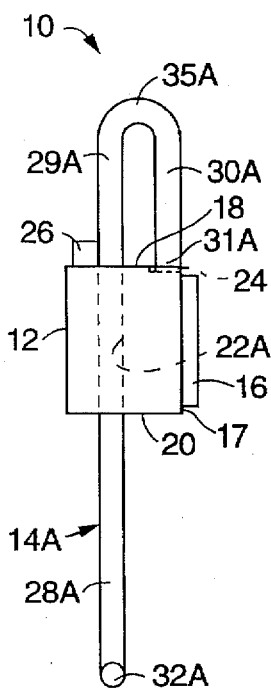
FIG. 4 is a side view of the intercostal retractor of FIG. 1, showing the retractor bars in the lifting position.
Figure 5:
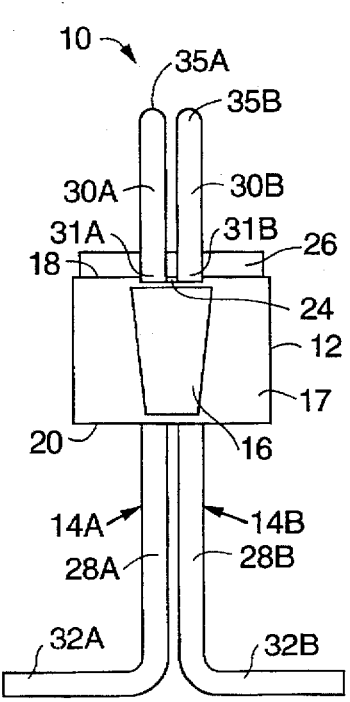
FIG. 5 is a front view of the intercostal retractor of FIG. 1, showing the retractor bars in the lifting position.

The position stop 26 helps to ensure that the retractor bars 32a, 32b are aligned with each other as they are inserted into the intercostal space. Alignment of the retractor bars 32a, 32b helps to reduce the likelihood that the retractor bars will snag tissue surrounding or underlying the incision during insertion. When the retractor arms 14a, 14b are in the insertion position, the tips 31a, 31b of the deployment bars 30a, 30b abut the position stop 26 as shown in FIGS. 1 and 2. During insertion of the retractor bars 32a, 32b through an incision, the user may hold the tips 31, 31b against the position stop 26 (such as by applying thumb pressure) to ensure that the retractor bars 32a, 32b remain in side-by-side relationship.

Figure 9:
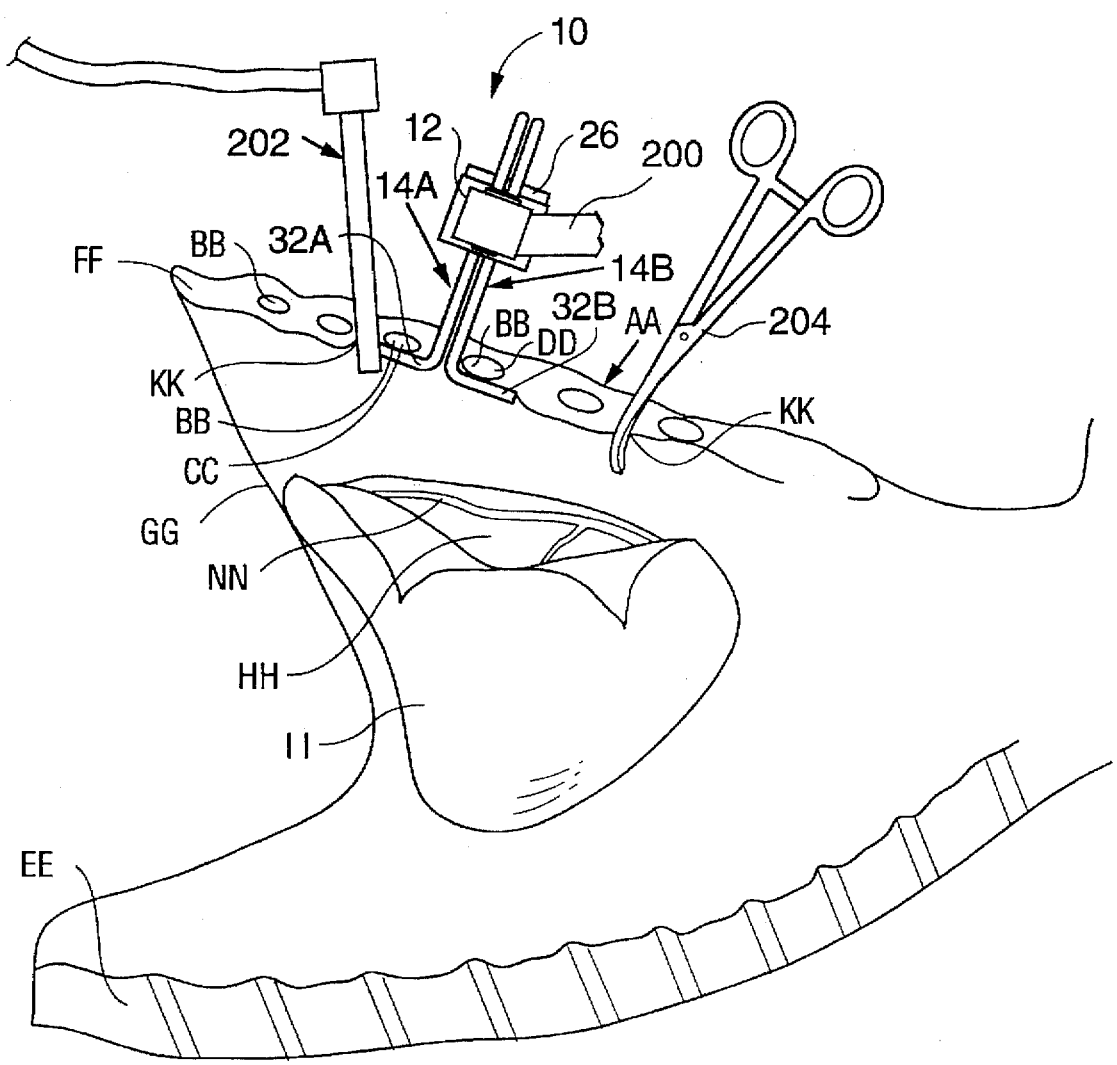
FIG. 9 is a cross-sectional view similar to FIG. 8, further showing insertion of surgical instruments through auxiliary incisions, and further showing dissection of the pericardium to expose the heart.
Figure 10:
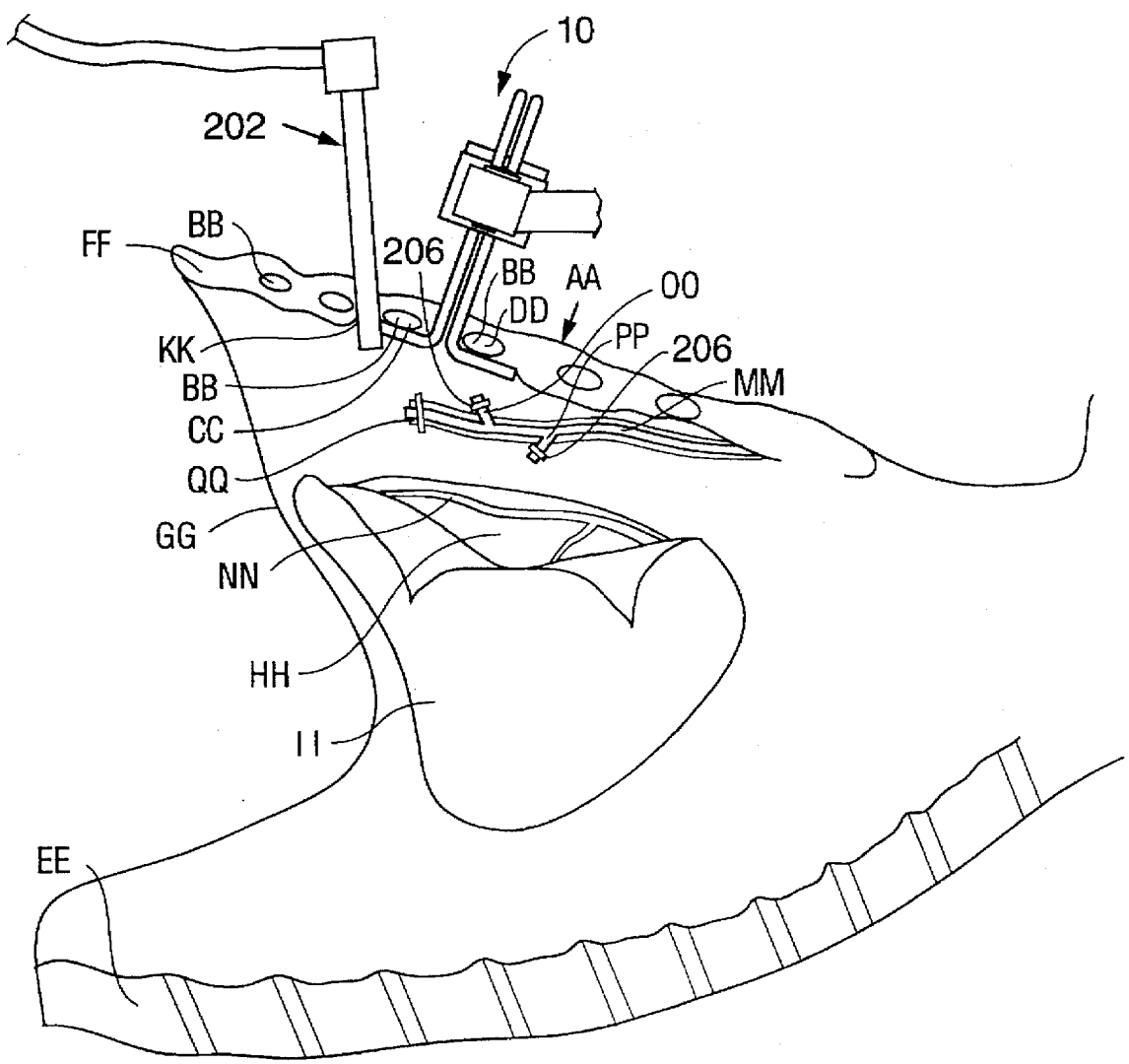
FIG. 10 is a cross-sectional view similar to FIG. 9, further showing insertion of an endoscope through an auxiliary incision and showing the pericardium dissected to expose the heart and coronary artery, and further showing the internal mammary artery dissected to form a bypass graft.

Use of the intercostal retractor of the present invention will next be described with reference to the representations of a thoracic cavity shown in FIGS. 7–10. These show a patient's sternum AA, ribs BB, spine EE, xiphoid process FF, and diaphragm GG. The heart is shown in FIGS. 9 and 10 and is designated HH; the pericardium, which encases the bean, is designated II. Intercostal space LL lies between the pericardium II and the sternum AA.

Figure 7:
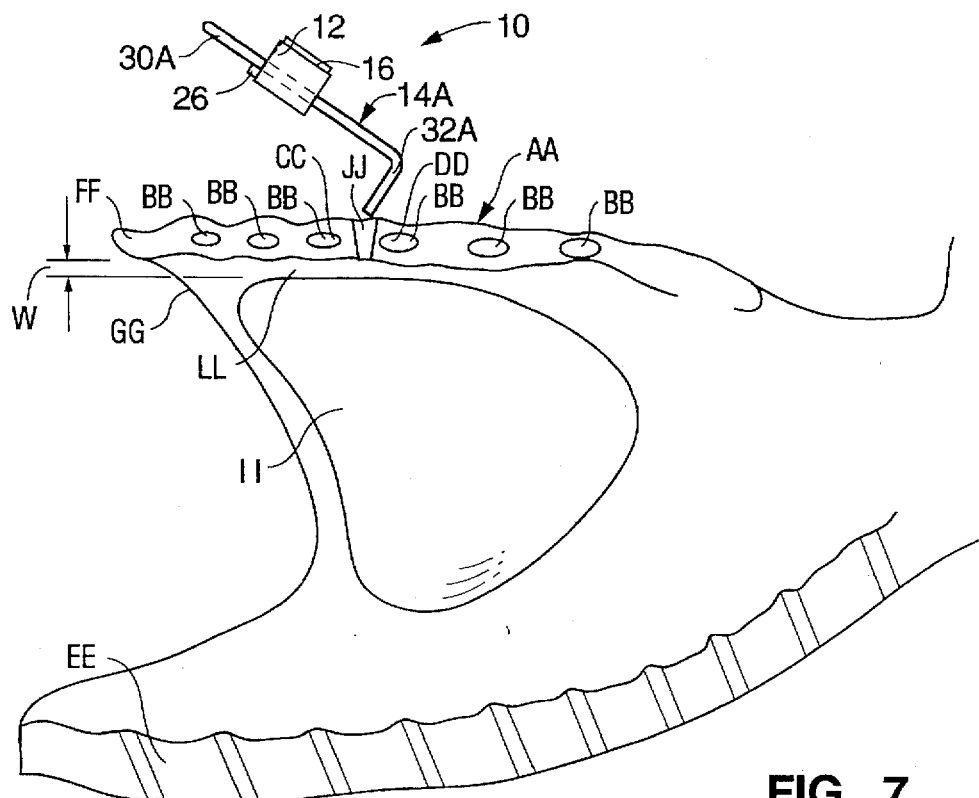
FIG. 7 is a cross-sectional view of the thoracic cavity, diagrammatically showing insertion of the retractor bars of the FIG. 1 retractor between a pair of ribs into the intercostal space.

For intercostal lifting, a small incision JJ (FIG. 7) of approximately 1–2 cm in length is made through the skin and tissue overlying the ribs BB. The incision JJ is preferably formed in a location that will enable insertion of the retractor bars 32a, 32b into the mediastinal space LL overlying the heart (through approximately the third intercostal space). An incision formed approximately 1 cm lateral to the sternum is suitable for this purpose. The deployment bars 30a, 30b of the retractor arms 14a, 14b are moved against the position stop 26 (best shown in FIGS. 1–2) to place the retractor bars 32a, 32b, in the insertion position (i.e. such that the retractor bars 32a, 32b, are close together and approximately parallel with each other). The retractor bars 32a, 32b are inserted through the incision JJ between a pair of adjacent ribs, which are specifically designated CC, and DD. A hooking motion, as depicted in FIG. 7, is used for insertion of the retractor bars 32a, 32b so that the retractor bars pass between the ribs CC, DD and into the space LL lying beneath the ribs CC, DD.

The deployment bars 30a, 30b of the retractor arms 14a, 14b are next rotated into the lifting position to rotate the retractor bars 32a, 32b such that they are separated by a rotational angle of 180°. The lifting body 12 is next rotated about its longitudinal axis through an angle of approximately 90° to align the retractor bars 32a, 32b in the sagittal plane, such that one bar contacts the superior rib (rib DD) and the other bar contacts the inferior rib (rib CC) as shown in FIG. 8.

Figure 8:
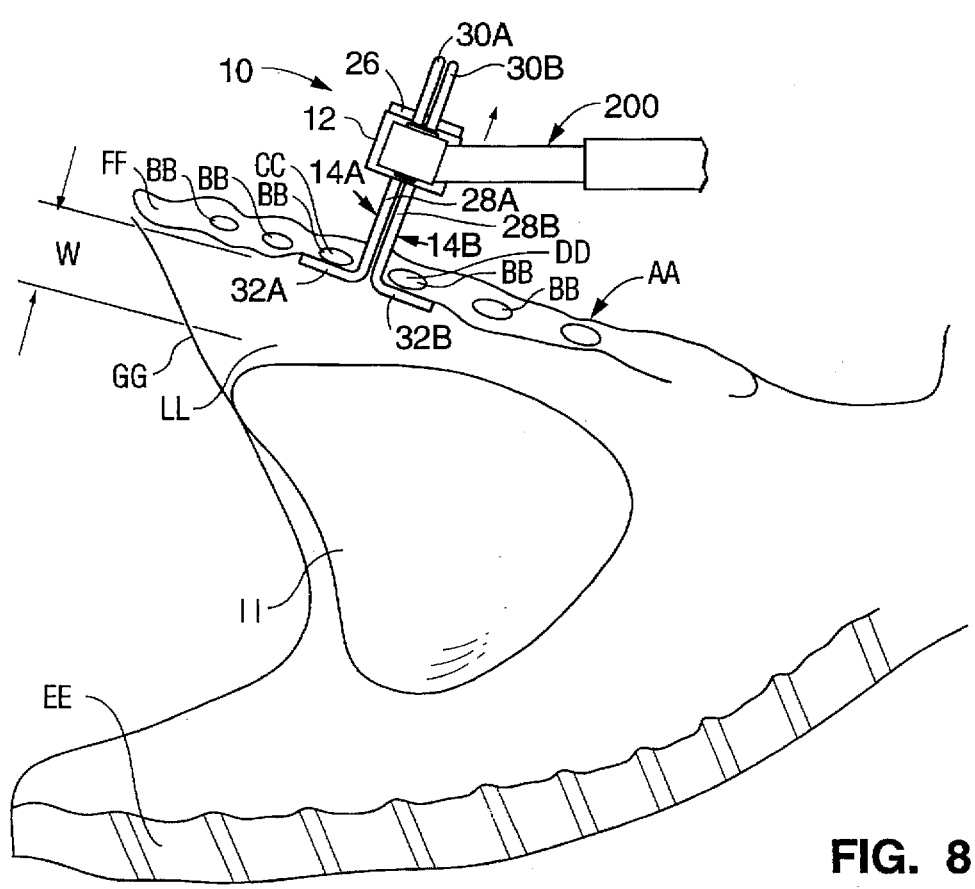
FIG. 8 is a cross-sectional view similar to FIG. 7, showing the retractor positioned in the sagittal plane, further showing the retractor bars each engaged with one of the fibs, and further showing application of a lifting force to the retractor by a mechanical lifting arm.

The dovetail connector 16 on the lifting body 12 is next connected to a mechanical lifting arm (designated 200 in FIG. 8) and a lifting force is applied in a direction substantially normal to plane of the ribs CC, DD as indicated by the arrow in FIG. 8. The retractor 10 may alternatively be lifted by hand and secured in an elevated position by means of a suspension system secured to a side rail of an operating table which supports the patient.

As can be seen in FIG. 8 the ribs are lifted to increase the width w of the mediastinal space LL so as to increase the working space between the pericardium II and the ribs BB and sternum AA.

Referring to FIG. 9, an endoscope 202 and surgical instruments, such as the curved scissors designated 204, may be inserted through additional small intercostal incisions KK. Instruments may alternatively be inserted through the same incision JJ through which the retractor bars 32a, 32b are inserted. Surgical access to the heart HH and coronary artery NN is gained by incising the pericardium II using the curved scissors 204.

During placement of an implantable cardiac pacemaker via a subxiphoid incision, an intercostal retractor according to the present invention may be used to lift the sternum AA and rib cage to expose the diaphragm and to provide a surgical approach through the diaphragm GG to the heart via a subxiphoid incision.

Referring to FIG. 10, the intercostal retraction technique just described is also useful for providing access to the internal mammary artery, which is used to bypass stenotic segments of the coronary artery during coronary artery bypass surgery. The internal mammary artery (designated MM in FIG. 10) extends behind the cartilages of the first six ribs BB, about 1.25 cm from the lateral border of the sternum AA.

To dissect the internal mammary artery MM, the intercostal retractor 10 is oriented as described above, and is positioned adjacent the sternum AA at a location that is approximately 2 cm lateral to the sternal border. Dissection instruments such as right angled clamps, curved scissors and an electrocautery probe (all not shown) may be introduced via the retractor incision site JJ or through ancillary intercostal ports KK.

An endoscope 202 (preferably one providing visualization at an angle of approximately 30°–45°) is inserted through an ancillary intercostal port KK to allow visualization of the region of the internal mammary artery MM. The pleura and the fascial layer (both not shown) coveting the artery are incised on either side of the internal mammary artery MM, and a pedicle (not shown) containing the internal mammary artery is dissected. To create a bypass graft, side branches (such as those designated OO and PP) of the internal mammary artery MM are individually clipped using a pair of spaced apart metal vascular clips 206 per side branch, and each side branch is transected between its respective clips. Dissection is carried out in this manner until a segment of the internal mammary artery MM is dissected that is of sufficient length for a bypass graft.

Next, distal end QQ of the internal mammary artery MM is clipped and transected. Vascular clips 206 on the side branches OO, PP may be replaced with suture ties (not shown) for increased occlusive stability. The pericardium II is next incised as described above to expose the coronary artery, designated NN in FIG. 10. Finally, the internal mammary artery MM is anastomosed to the coronary artery NN to bypass the stenotic segment or segments of the coronary artery NN.

Figure 11:
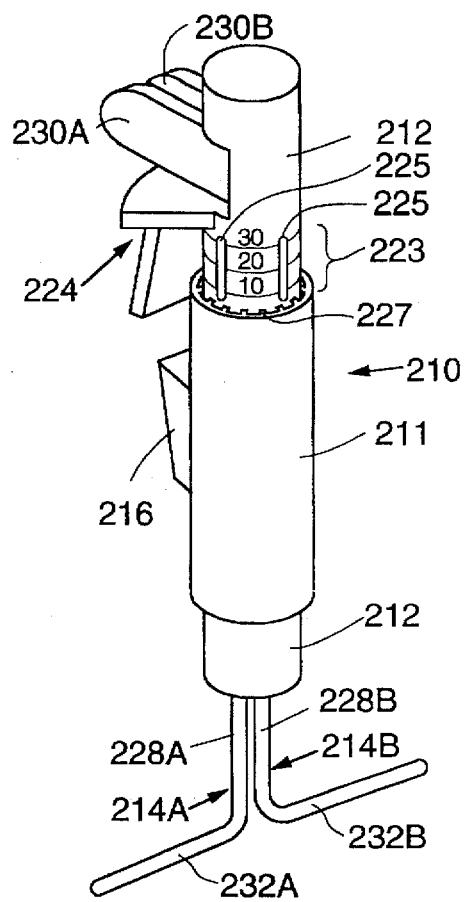
FIG. 11 is a perspective view of a second embodiment of a lifting retractor according to the present invention.

A second embodiment 210 of a mediastinal retractor according to the present invention is shown in FIG. 11. The second embodiment 210 is comprised generally of a lifting body 212, retractor arms 214a, 214b, and actuator levers 230a, 230b which rotate the retractor arms 214a, 214b. The retractor arms 214a, 214b are comprised of intermediate portions 228a, 228b and retractor bars 232a, 232b which extend laterally from their respective intermediate portions 228a, 228b.

As with the first embodiment, the retractor arms 214a, 214b of the second embodiment are rotatable between an insertion position and a lifting position. In the insertion position (which is similar to the position of the retractor arms 14a, 14b of the first embodiment 10 shown in FIG. 1), the retractor bars 232a, 232b are positioned in side-by-side relationship for insertion through an incision. In the lifting position, shown in FIG. 11, the retractor bars 232a, 232b are separated by a rotational angle of preferably 180°.

The remaining features of the second embodiment will be briefly described. Detailed descriptions of these features and their construction may be found in U.S. patent application Ser. No. 07/890,033, filed May 28, 1992, and U.S. patent application Ser. No. 08/128,427, filed Sep. 28, 1993, which are hereby incorporated by reference.

Rotation of the retractor arms 214a, 214b between the lifting and insertion positions is carried out through rotation of the actuator levers 230a, 230b. A locking mechanism 224 is provided which has a slot (not shown) which engages the actuator levers 230a, 230b when the retractor arms 214a, 214b are in the lifting position.

The retractor arms 214a, 214b are coupled to the lifting body 212, and the lifting body 212 is rotatably disposed within a sleeve 211. A dovetail mount 216 is mounted to the sleeve 211. The lifting body 212 is rotatable within the sleeve 211 (around the common longitudinal axis of the sleeve 211 and the lifting body 212).

The lifting body 212 is spring mounted within the sleeve 211 and is longitudinally slidable within the sleeve 211 when a tensile load is applied between the sleeve 211 and the retractor arms 214a, 214b. Keys 225 formed on the lifting body 212 engage with splines 227 formed in the sleeve 211 when the lifting body 212 slides in the distal direction by a predetermined distance. A spring (not shown) inside the sleeve 211 controls longitudinal sliding of the lifting body 212 so as to prevent engagement of the keys 225 and splines 227 until the tensile load on the retractor arms 214a, 214b reaches a predetermined level. A lifting force indicator 223 indicates the lifting force being applied during use.

The first and second embodiments are preferable because locking the arms 14a, 14b (or, with respect to the second embodiment, the arms 214a, 214b) with the retractor bars 32a, 32b (232a, 232b in the second embodiment) spaced 180° minimizes the effects of torsion on the arms 14a, 14b (214a, 214b) during lifting. However, alternative embodiments may be envisioned which employ a single legged retractor (e.g. a single right-angle retractor similar to a single one of the arms 14a, 14b which is passed between two ribs into the intercostal space and extended beneath the sternum) or a fan-type retractor having two arms that pivot to form an acute angle between them.

Figure 12:
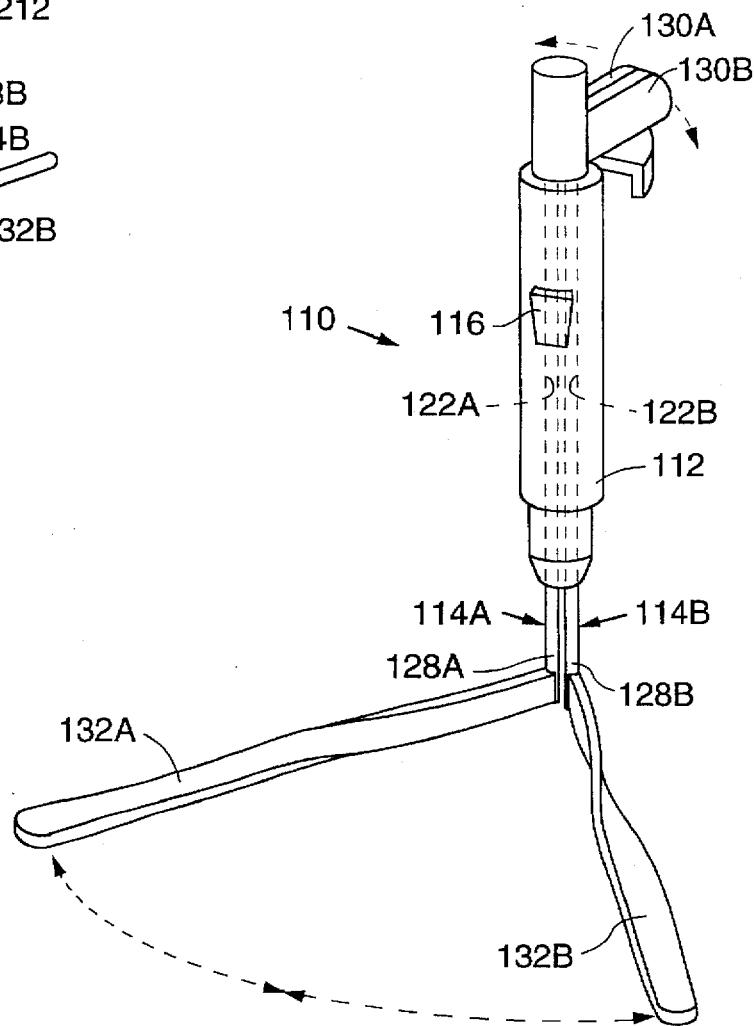
FIG. 12 is a perspective view of a third embodiment of a lifting retractor according to the present invention.

A third embodiment of a fan retractor 110, which may be used for subxiphoid or suprasternal lifting, is shown in FIG. 12 and will be briefly described. A detailed description of a fan retractor of this type appears in U.S. patent application 07/890,033 filed May 28, 1992, and is hereby incorporated by reference.

The fan retractor 110 has a lifting body 112 having a pair of throughbores 122a, 122b symmetrically offset from the longitudinal axis of the lifting body 112. Retractor arms 114a, 114b are rotationally positioned within the throughbores 122a, 122b.

The retractor arms 114a, 114b are comprised of intermediate portions 128a, 128b, retractor bars 132a, 132b, and deployment paddles 130a, 130b. The intermediate portions 128a, 128b are partially and rotatably disposed within the throughbores 122a, 122b, respectively. Retractor bars 128a, 128b extend laterally from the distal ends of the intermediate portions 128a, 128b, and deployment paddles 130a, 130b are attached to the proximal ends of the intermediate portions 128a, 128b.

The retractor bars 132a, 132b are rotatable between an open (lifting) position, shown in FIG. 12, in which they are separated by an acute rotational angle, and a closed (insertion) position (shown in FIGS. 13 and 14) in which the retractor bars 132a, 132b are positioned in close parallel relationship to permit their simultaneous insertion through a small (i.e. 1–2 cm) incision. Rotation of the retractor bars 132a, 132b is achieved by rotating the respective deployment paddles 130a, 130b as indicated by arrows in FIG. 12.

A dovetail connector 116 is preferably attached to the lifting body 112 for connecting the lifting body to a mechanical lifting arm such as the lifting arm 200 shown in FIG. 7.

A subxiphoid or suprasternal retractor may alternatively be provided with a single right angle retractor arm, such as the retractor arm 114a, fixed to the lifting body 112.

Figure 13:
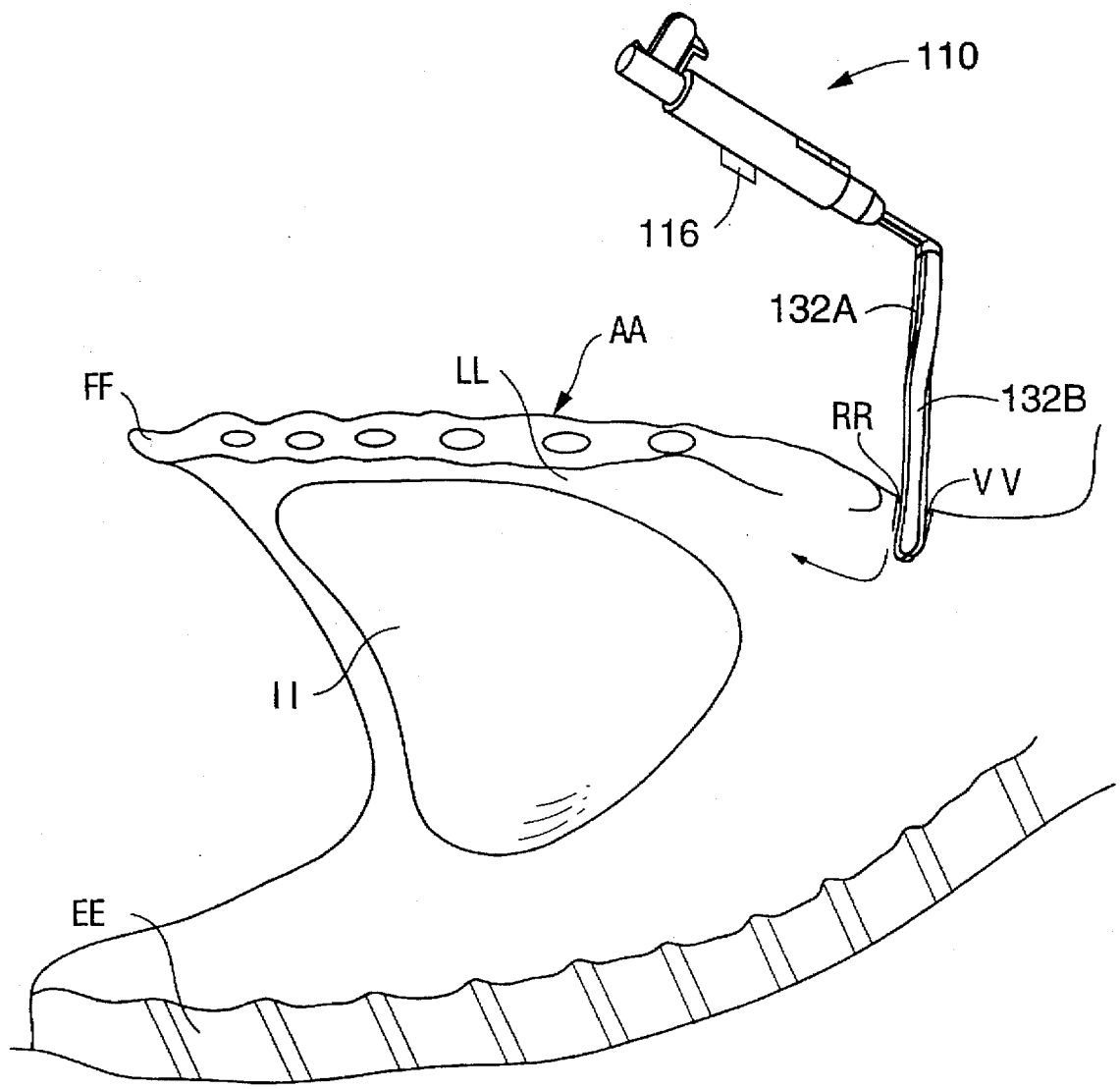
FIG. 13 is a cross-sectional view of the thoracic cavity, diagrammatically showing insertion of the FIG. 12 retractor through a suprasternal incision.

Referring to FIG. 13, to use the retractor of FIG. 12 for cardiac surgery using a suprasternal approach, a suprasternal incision RR is formed in the skin and underlying tissue, which are together designated VV. The retractor bars 132a, 132b are positioned in the closed position as shown, and are passed through the incision RR and into the mediastinal space LL, beneath the sternum AA. The retractor bars 132a, 132b are next rotated into the open position (which is shown in FIG. 12). The retractor 110 is lifted in the same manner shown in FIG. 8 with respect to the intercostal retractor, causing the retractor bars 132a, 132b to deliver a lifting force to the sternum AA. The retractor 110 is mounted via the dovetail mount 116 to a lifting device, such as the mechanical lifting arm shown in FIG. 8, to maintain lifting throughout the duration of the procedure.

Figure 14:
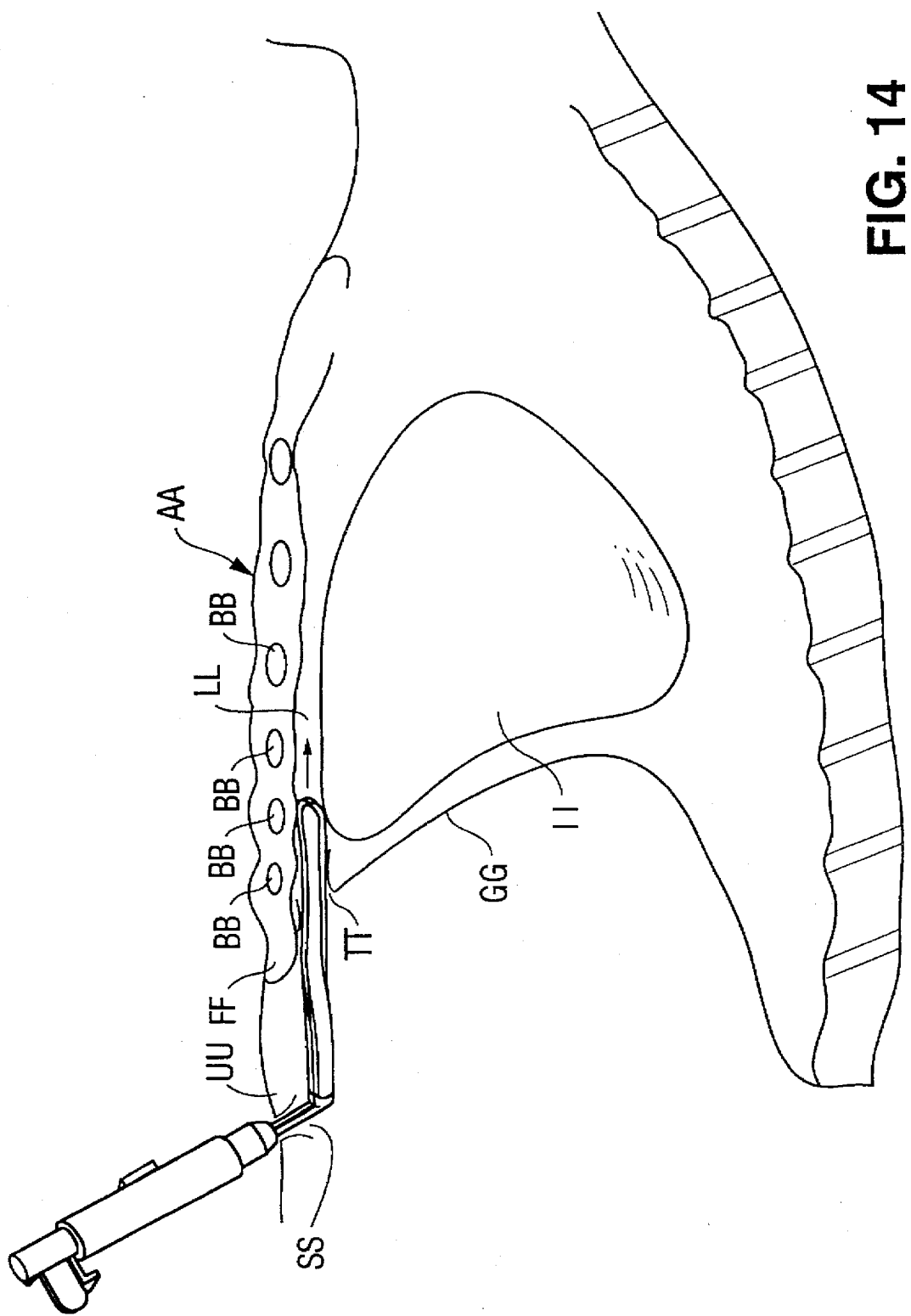
FIG. 14 is a cross-sectional view of the thoracic cavity, diagrammatically showing insertion of the FIG. 12 retractor through a subxiphoid incision and further through an incision in the diaphragm.

Use of the retractor of FIG. 12 using a subxiphoid approach is illustrated in FIG. 14. As there shown, the retractor bars 132a, 132b, which are initially in the insertion position, are passed through a subxiphoid incision SS formed in the skin and underlying tissue (collectively designated as UU) and subsequently through an opening TT formed in the diaphragm GG. The retractor bars 132a, 132b are next rotated into the open, lifting position shown in FIG. 12.

The retractor 110 is next lifted in the manner illustrated with respect to the intercostal retractor (FIG. 8), thereby imparting a lifting force to the sternum AA and ribs BB via the retractor bars 132a, 132b. The retractor 110 is mounted via the dovetail mount 116 to a lifting device, such as the mechanical lifting arm shown in FIG. 8, to maintain lifting throughout the duration of the procedure.

Because the third embodiment of a lifting retractor according to the present invention is designed to be inserted through a subxiphoid or suprasternal incision and positioned in contact with the sternum or with a number of adjacent ribs lateral of the sternum, the retractor bars 132a, 132b are preferably formed to have a greater length than the retractor bars 32a, 32b of the intercostal retractor. Retractor bars 132a, 132b of the alternative lifting retractor are preferably 4–6 inches in length.

Conclusion

While preferred embodiments of the invention have been illustrated and described, it should be understood that the invention is not limited to these embodiments, but rather is defined by the following claims.

What is claimed is:

1. A method of elevating a rib cage having ribs and a sternum to create a working space beneath the sternum and rib cage without performing a sternotomy, said method comprising the steps of:

(a) providing a retractor device having a first proximal portion and a first retractor bar joined in angular relation;

(b) forming a small incision in tissue adjacent to the rib cage;

(c) passing the first retractor bar through the incision, between a pair of the ribs which adjoin the sternum at one side of the sternum, and into a space beneath the rib cage, leaving the first proximal portion partially extending between the ribs and out of the space beneath the rib cage;

(d) positioning the first retractor bar beneath one of the ribs and engaging the rib cage with the retractor device;

(e) applying a lifting force to the first proximal portion of the retractor device to lift the rib cage and the sternum, thus creating a mediastinal working space within the rib cage; and (f) performing a surgical procedure within the mediastinal working space while maintaining the lifting force for the duration of the surgery.

2. The method of claim 1 wherein:

step (a) provides a retractor device having a lifting body, wherein the first proximal portion extends from the lifting body and forms a first lifting arm with the first retractor bar, and wherein the retractor device further includes a second lifting arm having a second proximal portion extending from the lifting body and a second retractor bar extending in angular relation to the second proximal portion, the first and second retractor bars pivotable about the longitudinal axes of their respective proximal portions; and steps (c) and (d) include the steps of (i) pivoting the first and second retractor bars into an insertion position wherein the first and second retractor bars are in close generally parallel relationship;

(ii) simultaneously passing the first and second retractor bars through the incision, between a pair of the ribs adjoining the sternum, and into a position wherein the first and second retractor bars are beneath the rib cage and their proximal portions extend between the ribs; and (iii) after step (ii), pivoting the first and second retractor bars into a lifting position wherein the first and second retractor bars are separated by a rotational angle and wherein each of the first and second retractor bars is positioned to engage one of the ribs upon application of the lifting force.

3. The method of claim 2 wherein step (iii) includes the step of pivoting the first and second retractor bars to a lifting position wherein the first and second retractor bars extend substantially longitudinally of one another.

4. The method of claim 1 wherein:

step (a) provides a retractor device having a lifting body, wherein the first proximal portion extends from the lifting body and is joined in angular relation to the first distal portion to form a first lifting arm with the first distal portion, and wherein the retractor device further includes a second lifting arm having a second proximal portion extending from the lifting body and a second distal portion extending in angular relation to the second proximal portion, the first and second distal portions pivotable about the longitudinal axes of their respective proximal portions; and steps (c) and (d) include the steps of
(i) pivoting the first and second distal portions into an insertion position wherein the first and second distal portions are in close generally parallel relationship;
(ii) simultaneously passing the first and second distal portions through the incision, between a pair of the ribs adjoining the sternum, and into a position wherein the first and second distal portions are beneath the rib cage and their proximal portions extend between the ribs; and
(iii) after step (ii), pivoting the first and second distal portions into a lifting position wherein the first and second distal portions are separated by a rotational angle and wherein each of the first and second distal portions is positioned to engage one of the ribs upon application of the lifting force.

5. The method of claim 1 wherein:

step (a) provides a retractor device having a lifting body, wherein the first proximal portion extends from the lifting body and is joined in angular relation to the first distal portion to form a first lifting arm with the first distal portion, and wherein the retractor device further includes a second lifting arm having a second proximal portion extending from the lifting body and a second distal portion extending in angular relation to the second proximal portion, the first and second distal portions pivotable about the longitudinal axes of their respective proximal portions; and steps (c) and (d) include the steps of
(i) pivoting the first and second distal portions into an insertion position wherein the first and second distal portions are in close generally parallel relationship;
(ii) simultaneously passing the first and second distal portions through the first incision, through the second incision, between a pair of the ribs adjoining the sternum, and into a position wherein the first and second distal portions are beneath the rib cage and their proximal portions extend between the ribs; and
(iii) after step (ii), pivoting the first and second distal portions into a lifting position wherein the first and second distal portions are separated by a rotational angle and wherein each of the first and second distal portions is positioned to engage one of the ribs upon application of the lifting force.

6. A method of elevating a rib cage having ribs and a sternum to create a working space beneath the sternum and rib cage without performing a sternotomy, said method comprising the steps of:

(a) providing a retractor device having a distal portion and a proximal portion joined in angular relation;

(b) forming a small incision in tissue adjacent to the rib cage;

(c) passing the distal portion of the retractor device through the incision, between a pair of the ribs which adjoin the sternum at one side of the sternum, and into a space beneath the rib cage, leaving the proximal portion partially extending between the ribs and out of the space beneath the rib cage, and (d) positioning the distal portion beneath one of the ribs and engaging the rib cage with the retractor device;

(e) applying a lifting force to the proximal portion of the retractor device to lift the rib cage and the sternum, thus creating a mediastinal working space within the rib cage;

(f) while maintaining the lifting force, performing a surgical procedure utilizing surgical instruments introduced into the mediastinal working space between a pair of the ribs which adjoin the sternum at one side of the sternum.

7. A method of elevating a rib cage having ribs and a sternum to create a working space beneath the sternum and rib cage without performing a sternotomy, said method comprising the steps of:

(a) providing a retractor device having a lifting body, a first lifting arm having a proximal portion extending from the lifting body and a first retractor bar extending in angular relation to the proximal portion, and a second lifting arm having a proximal portion extending from the lifting body and a second retractor bar extending in angular relation to the proximal portion, the first and second retractor bars pivotable about the longitudinal axes of their respective proximal portions;

(b) forming a small incision in tissue adjacent to the rib cage;

(c) pivoting the first and second retractor bars into an insertion position wherein the first and second retractor bars are in close generally parallel relationship;

(d) simultaneously passing the first and second retractor bars through the incision, between a pair of the ribs which adjoin the sternum at one side of the sternum, and into a position wherein the first and second retractor bars are beneath the rib cage and their proximal portions extend between the ribs; and (e) after step (d), pivoting the first and second retractor bars into a lifting position wherein the first and second retractor bars are separated by a rotational angle and wherein each of the first and second retractor bars is positioned to engage one of the ribs upon application of the lifting force;

(f) applying a lifting force to the proximal portion of the retractor device to lift the rib cage and the sternum, thus creating a mediastinal working space within the rib cage;

(g) while maintaining the lifting force, performing a surgical procedure utilizing surgical instruments introduced into the mediastinal working space between a pair of the ribs which adjoin the sternum at one side of the sternum.

8. The method of claim 7 further comprising the step of locking the retractor arms in the lifting position prior to application of the lifting force.

* * * * *